United States Patent [19]
Chen et al.

[11] Patent Number: 5,848,322
[45] Date of Patent: Dec. 8, 1998

[54] SERIES CAPACITOR INK SENSOR FOR MONITORING LIQUID DEVELOPER MATERIAL

[75] Inventors: Inan Chen; Joseph Mort, both of Webster, N.Y.; Mary Ann Machonkin, Homosassa, Fla.

[73] Assignee: Xerox Corporation, Stamford, Conn.

[21] Appl. No.: 4,760

[22] Filed: Jan. 8, 1998

[51] Int. Cl.[6] .................................................. G03G 15/10
[52] U.S. Cl. ............................................ 399/57; 324/71.1
[58] Field of Search ........................ 399/29, 57; 324/71.1, 324/464, 713; 430/112, 105

[56] References Cited

U.S. PATENT DOCUMENTS

| 4,928,065 | 5/1990 | Lane et al. ................................ 324/464 |
| 5,302,482 | 4/1994 | Elmasry et al. ..................... 430/112 X |

FOREIGN PATENT DOCUMENTS 57-58176  4/1982  Japan.

*Primary Examiner*—Arthur T. Grimley
*Assistant Examiner*—Sophia S. Chen
*Attorney, Agent, or Firm*—D. A. Robitaille

[57] ABSTRACT

An apparatus for determining charge density and mobility in a liquid solution having electrically charged particles therein. The apparatus includes an electrode, and a dielectric member having a first surface situated opposite the electrode for providing a volume therebetween in which a sample of the liquid may be placed. A fixed bias voltage applied to the electrode to produce an electrical current flow through the liquid solution and the dielectric member. A device coupled to the dielectric member, measures the electrical current as a function of time to provide a measure of voltage decay across the liquid solution. The voltage decay corresponds to the charge density of the liquid solution.

12 Claims, 7 Drawing Sheets

SERIES CAPACITOR INK SENSOR FOR MONITORING LIQUID DEVELOPER MATERIAL

This invention relates generally to an electrostatographic printing machine, and more particularly concerns an apparatus for monitoring total density of toner charge and the mobility thereof in a liquid developer material in a liquid developing material-based copying or printing machine.

Generally, the process of electrostatographic copying is initiated by exposing a light image of an original document to a substantially uniformly charged photoreceptive member. Exposing the charged photoreceptive member to a light image discharges the photoconductive surface thereof in areas corresponding to non-image areas in the original input document while maintaining the charge in image areas, resulting in the creation of an electrostatic latent image of the original document on the photoreceptive member. This latent image is subsequently developed into a visible image by a process in which developer material is deposited onto the surface of the photoreceptive member. Typically, this developer material comprises carrier granules having toner particles adhering triboelectrically thereto, wherein the toner particles are electrostatically attracted from the carrier granules to the latent image for forming a powder toner image on the photoreceptive member. Alternatively, liquid developer materials comprising a liquid carrier material having toner particles dispersed therein have been utilized, wherein the liquid developer material is applied to the latent image with the toner particles being attracted toward the image areas to form a liquid image. Regardless of the type of developer material employed, the toner particles of the developed image are subsequently transferred from the photoreceptive member to a copy sheet, either directly or by way of an intermediate transfer member. Once on the copy sheet, the image may be permanently affixed to provide a "hard copy" reproduction of the original document or file. In a final step, the photoreceptive member is cleaned to remove any charge and/or residual developing material from the photoconductive surface in preparation for subsequent imaging cycles.

The above described electrostatographic reproduction process is well known and is useful for light lens copying from an original, as well as for printing applications involving electronically generated or stored originals. Analogous processes also exist in other printing applications such as, for example, digital laser printing where a latent image is formed on the photoconductive surface via a modulated laser beam, or ionographic printing and reproduction where charge is deposited on a charge retentive surface in response to electronically generated or stored images. In addition, variant processes are also known, wherein the electrostatic latent image is formed directly in a toner layer, with image areas and non-image areas subsequently separate to produce a developed image. Some of these printing processes develop toner on the discharged area, known a DAD or "write black" systems, in contradistinction to the light lens generated image systems which develop toner on the charged areas, known as CAD, or "write white" systems. The subject invention applies to both such systems.

The use of liquid developer materials in imaging processes is well known. Likewise, the art of developing electrostatographic latent images with liquid developer materials is also well known. Indeed, various types of liquid developing material development systems have heretofore been disclosed.

Liquid developers have many advantages. For example, images developed with liquid developers can be made to adhere to paper without a fixing or fusing step, thereby eliminating a requirement to include a resin in the liquid developer for fusing purposes. In addition, the toner particles can be made to be very small without resulting in problems often associated with small particle toners, such as airborne contamination which can adversely affect machine reliability and can create potential health hazards. The use of very fine toner particles enable the production of higher quality images than those generally formed with dry toners. In full color imaging processes, production of a texturally attractive output document is enabled through the use of liquid developers due to minimal multilayer toner height build-up (whereas full color images developed with dry toners often exhibit substantial height build-up of the image in regions where color areas overlap). In addition, full color imaging with liquid developers is economically attractive, particularly if surplus liquid carrier containing the toner particles can be economically recovered without cross contamination of colorants. Further, full color prints made with liquid developers can be processed to a substantially uniform finish, whereas uniformity of finish is difficult to achieve with powder toners due to variations in the toner pile height as well as a need for thermal fusion, among other factors.

Although specific liquid development systems may vary, one well known type of system includes a roll member adapted to transport liquid developer material into a position proximate to a surface to be coated. In such systems, is the roll member is typically partly submerged in a sump of liquid developer material with the roll member being rotated at a sufficiently high velocity so as to transport the liquid developer to the surface in the form of a relatively thin toner layer formed along the surface of the roll member. In addition, an electrical bias may be applied to the roll member for generating an electrical field across a gap between the roll member and the surface to maintain a toning meniscus across the gap so as to provide a desired density of toner particles entrained in the liquid developer and to reduce undesirable background staining of the photoreceptor as it passes the developer apparatus.

Generally, in the field of electrostatographic printing and copying, development of a latent image takes place at high speeds, which requires that a large amount of uniformly characteristic liquid developer material be supplied to the photoconductive surface as uniformly as possible to produce a high quality image without any variations in the development thereof. Accordingly, it has been found, that it is advantageous to monitor the process of applying the liquid developer material to detect any property variations that are relevant to the development process. The present invention provides an ink sensor for separately monitoring the total density of toner charge and its mobility in the developer material. The sensor is applicable to undiluted inks or their component charge director solutions alike. By combining a simple and rugged cell design with standard pulse height electronics, both of low cost, the sensor has broad applicability and value for image quality control in liquid ink development based products. The following publication may be particularly relevant; "Space-Charge-Perturbed Electrophoresis in Nonpolar Colloidal Dispersions", J. Appl. Physics, Vol. 80, No. 12, Dec. 15, 1996. The foregoing article is specifically incorporated into the present disclosure by reference.

In accordance with one aspect of the present invention, there is provided an apparatus for determining charge density and mobility in a liquid solution having electrically charged particles therein. The apparatus includes an electrode. A dielectric member having a first surface situated opposite the electrode provides for a volume therebetween in which a sample of the liquid may be placed. A fixed bias voltage is applied to the electrode to produce an electrical current flow through the liquid solution and the dielectric member. Means coupled to the dielectric member measure the electrical current as a function of time to provide a measure of voltage decay across the liquid solution. The voltage decay corresponds to the charge density of the liquid solution.

In accordance with another aspect of the present invention, there is provided a sensor for determining charge density and mobility in a liquid developer comprising liquid carrier and electrically charged toner particles therein. The sensor includes an electrode. A dielectric member having a first surface situated opposite the electrode provides for a volume therebetween in which a sample of the liquid may be placed. A fixed bias voltage is applied to the electrode to produce an electrical current flow through the liquid solution and the dielectric member. Means coupled to the dielectric member measure the electrical current as a function of time to provide a measure of voltage decay across the liquid solution. The voltage decay corresponds to the charge density of the liquid solution.

In accordance with yet another aspect of the present invention, there is provided an electrostatographic printing machine of the type having a liquid developer comprising liquid carrier and electrically charged toner particles therein. The improvement includes an electrode. A dielectric member having a first surface situated opposite the electrode provides for a volume therebetween in which a sample of the liquid may be placed. A fixed bias voltage is applied to the electrode to produce an electrical current flow through the liquid solution and the dielectric member. Means coupled to the dielectric member measure the electrical current as a function of time to provide a measure of voltage decay across the liquid solution. The voltage decay corresponds to the charge density of the liquid solution.

Other aspects of the present invention will become apparent as the following description proceeds and upon reference to the drawings, in which.

Figure 3:
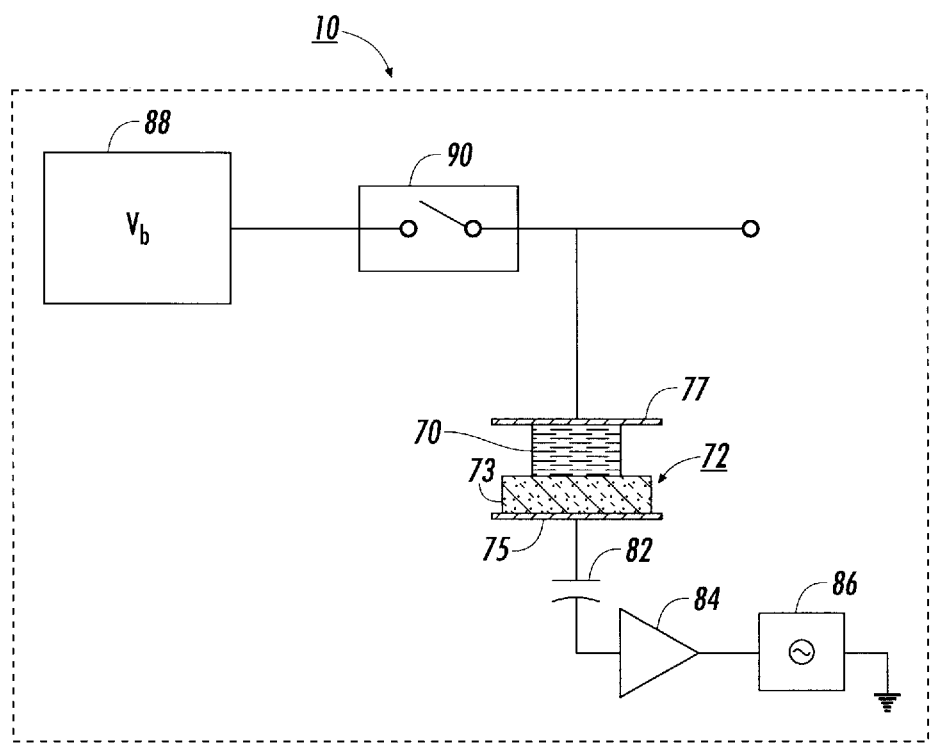
Figure 4:
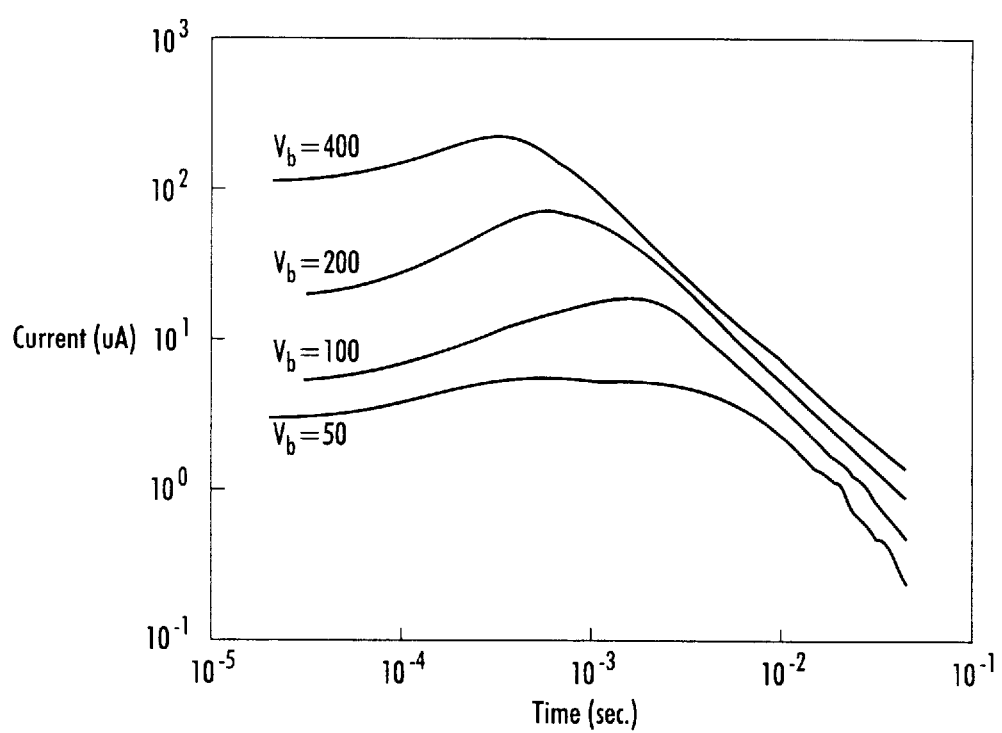
Figure 5:
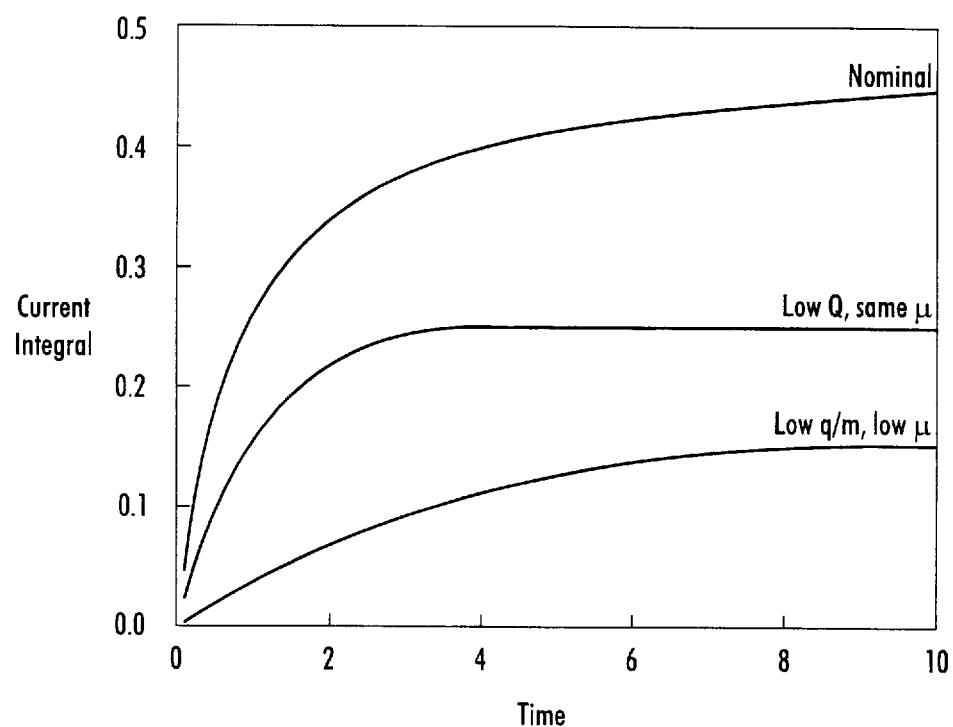
Figure 6:
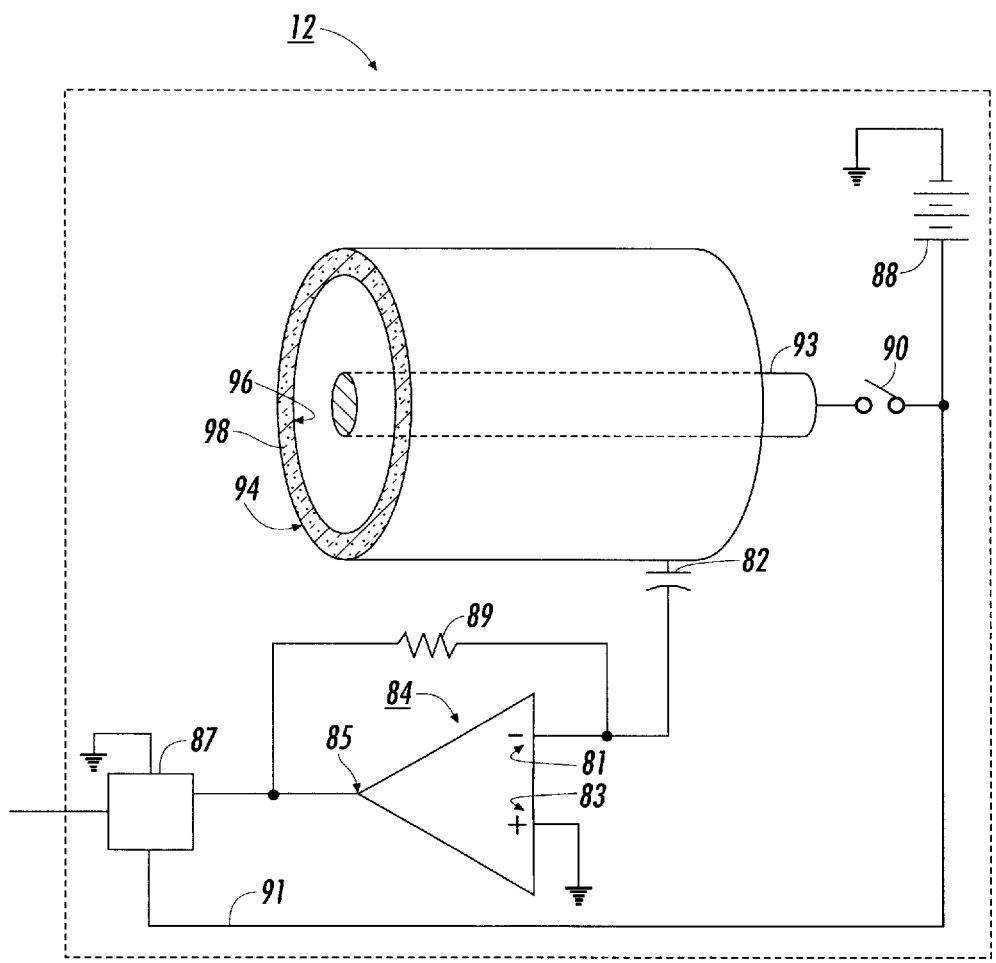
Figure 7:
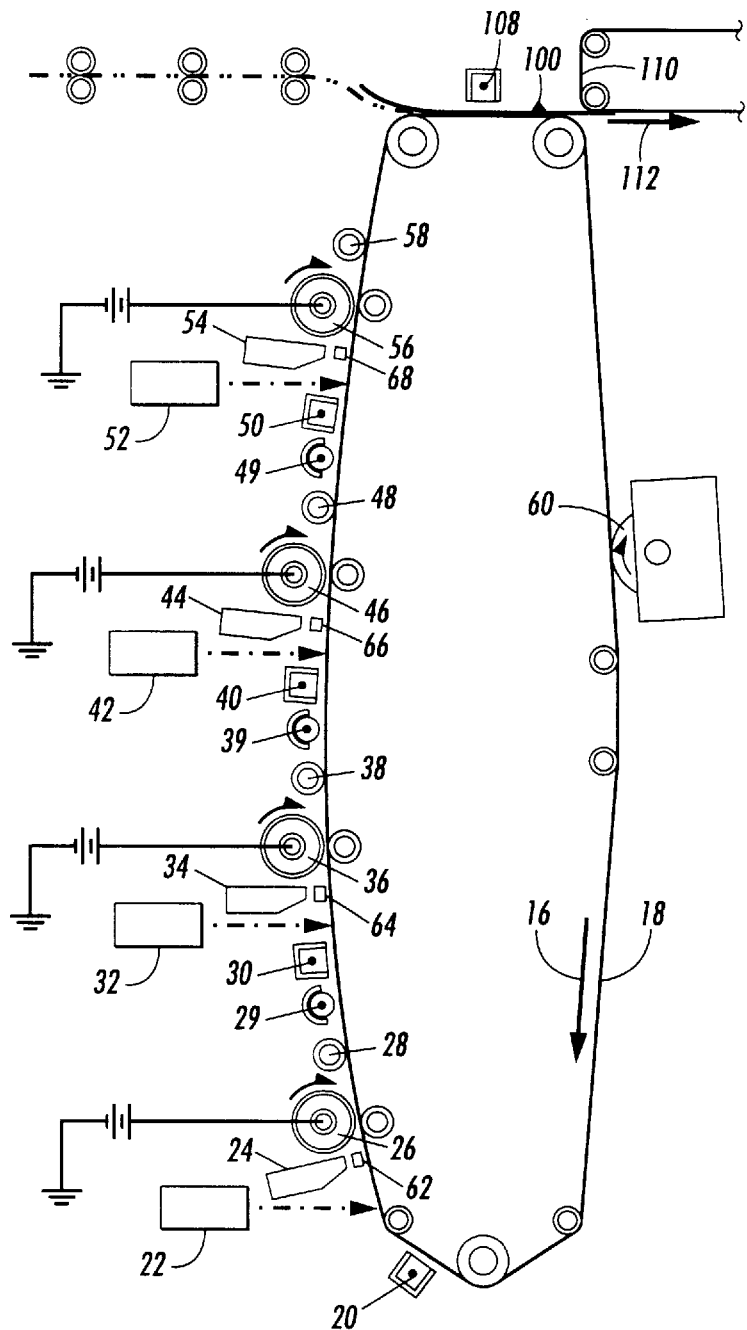

FIG. 3 schematically illustrates an electrical circuit that simulates the electrophoresis occurring in electrographic development;

FIG. 4 shows current versus time curves of a typical liquid developer material tested in the FIG. 3 embodiment, at various bias voltages (Vb);

FIG. 5 shows changes in toner concentration or toner charge/mass ratio as a current integral versus time relationship;

FIG. 6 is schematic illustration of a series-capacitor sensor in accordance with the present invention designed for use in electrostatographic printing machines; and FIG. 7 is schematic, elevational view of a color electrostatographic printing machine utilizing the series-capacitor sensor of the present invention.

For a general understanding of the features of the present invention, reference is made to the drawings, wherein like reference numerals have been used throughout to designate identical elements. FIG. 7 is a schematic elevational view illustrating an exemplary full-color, single-pass, image-on-image, liquid developing material based electrostatographic printing machine incorporating the features of the present invention. It will become apparent from the following discussion that the apparatus of the present invention may be equally well-suited for use in a wide variety of printing processes and machine architectures such that the present invention is not necessarily limited in its application to the particular electrostatographic process or system described herein. Thus, although the present invention will be described in connection with a preferred system environment and embodiment thereof, it will be understood that the description of the invention is not intended to limit the invention to this preferred environment and/or embodiment. Indeed, the description is intended to cover all alternatives, modifications, and equivalents as may be included within the spirit and scope of the invention as defined by the appended claims.

Turning now to FIG. 7, inasmuch as the art of electrostatographic printing is well known, the various processing stations will be described briefly with reference thereto. The liquid developing material based multicolor electrostatographic printing machine employs a photoreceptor 18 in the form of a continuous multilayered belt member, generally comprising a photoconductive surface deposited on an electrically grounded conductive substrate. The photoreceptor 18 is entrained about a plurality of rollers, at least one of which is rotatably driven by a drive mechanism (not shown) for advancing the belt along a curvilinear path in the direction of arrow 16, such that successive portions of the photoreceptive belt 18 can be transported through the various processing stations disposed about the path of movement thereof.

The electrostatographic printing process is initiated by applying a substantially uniform charge to the photoreceptive surface of photoreceptor 18. As such, an initial processing station is shown as a charging station, including a corona generating device 20. The corona generating device 20 is capable of applying a relatively high and substantially uniform charge potential to the surface of the photoreceptor belt 18.

After the substantially uniform charge is placed on the surface of photoreceptor belt 18, the electrostatographic printing process proceeds by either imaging an input document placed on the surface of a transparent imaging platen (not shown), or by providing a computer generated image signal, for selectively discharging the photoconductive surface in accordance with the image to be generated. For multicolor printing and copying, the imaging process involves separating the imaging information into the three primary colors plus black to provide a series of subtractive imaging signals, with each subtractive imaging signal being proportional to the intensity of the incident light of each of the primary colors or black. These imaging signals are then transmitted to a series of individual raster output scanners (ROSs), shown schematically by reference numerals 22, 32, 42 and 52, for generating complementary color-separated latent images on the charged photoreceptive belt 18. Typically, each ROS 22, 32, 42 and 52 writes the latent image information in a pixel by pixel manner.

Each of these color-separated electrostatic latent images are serially developed into visible images on the photoreceptive belt 18 via coating flow applicators identified by reference numerals 24, 34, 44 and 54. Each coating flow applicator operates as an apparatus for transporting liquid developing material and for applying a thin coating layer of liquid developing material to the surface of belt 18. Adjacent to each of the flow applicators is a series-capacitor sensor of the present invention. Each of these sensors, identified by reference numerals 62, 64, 66, and 68, separately monitor the total charge density and mobility thereof in the developer material applied to the belt surface. The sensor will be described in grater detail following the instant description of the electrostatographic printing system of FIG. 7.

Each coating flow applicator transports a different color developer material into contact with a different electrostatic latent image on the photoreceptor surface for developing the latent image with pigmented toner particles, and creating a visible image. By way of example, coating flow applicator 24 transports cyan colored liquid developer material, coating flow applicator 34 transports magenta colored liquid developer material, coating flow applicator 44 transports yellow colored liquid developer material, and coating flow applicator 54 transports black colored liquid developer material. Each different color liquid developing material comprises pigmented toner particles immersed in a liquid carrier medium, wherein the toner particles are charged to a polarity opposite in to the latent image on the photoconductive surface of belt 18 such that the toner particles are attracted to the electrostatic latent image to create a visible developed image thereof.

Generally, in a liquid developing material-based system, the liquid carrier medium makes up a large amount of the liquid developer composition. Specifically, the liquid medium is usually present in a range of from about 80 to about 98 percent by weight in the developing material, although this amount may vary outside of the stated range. By way of example, the liquid carrier medium may be selected from a wide variety of materials, including, but not limited to, any of several hydrocarbon liquids, such as high purity alkanes having from about 6 to about 14 carbon atoms, exemplified by such commercial products as Norpar® 12; Norpar® 13 and Norpar® 15, as well as isoparaffinic hydrocarbons such as Isopar® G, H, L, and M, available from Exxon Corporation. Other examples of materials suitable for use as a liquid carrier include Amsco® 460 Solvent, and Amsco® OMS, available from American Mineral Spirits Company, Soltrol®, available from Phillips Petroleum Company, Pagasol®, available from Mobil Oil Corporation, Shellsol®, available from Shell Oil Company. Isoparaffinic hydrocarbons may provide a preferred liquid media since they are colorless, environmentally safe, and possess a sufficiently high vapor pressure so a thin film of the liquid evaporates from the contacting surface within seconds at ambient temperatures.

The toner particles utilized in liquid developer compositions can be any pigmented particle compatible with the liquid carrier medium, such as, for example those disclosed in U.S. Pat. Nos. 3,729,419; 3,841,893; 3,968,044; 4,476,210; 4,707,429; 4,762,764; 4,794,651; 5,066,559 and 5,451,483, among various other patents and disclosures known to one of skill in the art. Preferably, the toner particles have an average particle diameter from about 0.2 to about 10 microns, and more preferably in the range from about 0.5 to about 2 microns. In addition, the toner particles may be present in amounts of from about 1 to about 10 percent by weight, and preferably from about 1 to about 4 percent by weight of the developer composition. The toner particles can consist solely of pigment particles, or may comprise a resin and a pigment; a resin and a dye; or a resin, a pigment, and a dye. Suitable resins include poly(ethyl acrylate-co-vinyl pyrrolidone), poly(N-vinyl-2-pyrrolidone), and the like. Suitable dyes include Orasol Blue 2GLN, Red G, Yellow 2GLN, Blue GN, Blue BLN, Black CN, Brown CR, all available from Ciba-Geigy, Inc., Mississauga, Ontario, Morfast Blue 100, Red 101, Red 104, Yellow 102, Black 101 Black 108, all available from Morton Chemical Company, Ajax, Ontario. Dyes generally are present in an amount of from about 5 to about 30 percent by weight of the toner particle, although other amounts may be present provided that the objectives of the present invention are achieved. Suitable pigment materials include carbon blacks such as Microlith® CT, available from BASF, Printex® 140 V, available from Degussa, Raven® 5250 and Raven® 5720, available from Colombian Chemicals Company. Pigment materials may be colored, and may include magenta pigments such as Hostaperm Pink E (American Hoechst Corporation) and Lithol Scarlet (BASF), yellow pigments such as Diarylide Yellow (Dominion Color Company), cyan pigments such as Sudan Blue OS (BASF), and the like. Generally, any pigment material is suitable provided that it consists of small particles that combine well with any polymeric material also included in the developer composition. Pigment particles are generally present in amounts of from about 10 to about 40 percent by weight of the toner particles, and preferably from about 10 to about 30 percent by weight.

In addition to the liquid carrier vehicle and toner particles which typically make up the liquid developer materials, a charge control additive, sometimes referred to as a charge director, is also included for facilitating and maintaining a uniform charge on toner particles by imparting an electrical charge of selected polarity (positive or negative) to the toner particles. Examples of suitable charge control agents include lecithin, available from Fisher Inc.; OLOA 1200, a polyisobutylene succinimide, available from Chemical Company; basic barium petronate, available from Witco Inc.; zirconium octoate, available from Nuodex; as well as various forms of aluminum stearate; salts of calcium, manganese, magnesium and zinc; heptanoic acid; salts of barium, aluminum, cobalt, manganese, zinc, cerium, and zirconium octoates and the like. The charge control additive may be present in an amount of from about 0.01 to about 3 percent by weight, and preferably from about 0.02 to about 0.05 percent by weight of the developer composition.

Returning to a description of the process carried out by the system of FIG. 7, the amount of liquid developing material, and in particular the liquid carrier portion of the liquid developing material that is deposited on the surface of the photoreceptor belt 18 is preferably reduced by an incipient amount during or after image development. To this end, metering rollers 26, 36, 46 and 56 are positioned slightly downstream of, and adjacent to, respective developing material coating flow applicators 24, 34, 44 and 54, in the direction of movement of the photoreceptor 18. Preferably, the peripheral surface of each metering roller is situated in close proximity to the surface of the photoreceptor 18 and may or may not contact the surface of the photoreceptor 18 and/or the liquid layer thereon. In addition, the peripheral surface of the metering roller 26 is preferably rotated in a direction opposite the path of movement of the photoreceptor in order to create a substantial shear force against the thin layer of liquid developing material present between it and the photoreceptor 18. This shear force removes a predetermined amount of excess developing material, in particular carrier liquid, from the surface of the photoreceptor and transports this excess developing material in the direction of the developing material flow applicator 24, with the excess developing material eventually falling away from the rotating metering roll 26 for collection in a sump (not shown) or other liquid developer collection and reclaim system.

As shown, the metering rolls 26, 36, 46 and 56 are electrically biased by supplying DC voltage thereto for repelling or attracting toner particles present in the liquid developing material on the photoreceptor belt 18. It will be recognized that, by providing a predetermined electrical bias at the metering roll of the same charge polarity as the charge on the developed image, removal of deposited toner particles from the surface of the photoreceptor due to the shear forces created by the movement of the metering roll can be inhibited. Conversely, by providing a predetermined electrical bias to the metering roll which is opposite in polarity to the charge of the developed image, excess toner material or background image removal can be induced, if desired.

After the above-described metering process is completed, the developed liquid image on the photoconductor may preferably be further processed or "conditioned" to pack or condense the image onto the surface of the photoreceptor and to further remove some of the liquid carrier therefrom. This basic concept is shown, for example, by previously cited U.S. Pat. No. 4,286,039, as well as U.S. Pat. Nos 4,974,027 and 5,028,964, among various other patents. Thus, an image conditioning system may be utilized for conditioning a developed liquid image on a photoreceptor surface or on any surface which is used to transport a developed image (e.g. an intermediate transfer belt), or for conditioning any liquid developer layer on the photoreceptor surface or other surface, whereby the liquid developer is first subjected to a large electric field for electrostatically driving the colorant containing toner particles of the liquid developer toward the surface, followed by removal of excess liquid from the liquid developer layer on the belt surface. In either method of use, an ink conditioning system is shown at reference numerals 28, 38, 48, and 58, wherein a biased roller is urged against the photoreceptor 18 to electrostatically compress the liquid developer on the photoreceptor belt 18 while further removing excess liquid therefrom. It will be recognized that various methods for forming high electric fields, such as a corona generating device, an electrically biased non-contact blade member, a charging "shoe", or a non-contact biased roller, can also be used in combination with a non-biased contact roller as an alternative to the described conditioning apparatus.

Following developer conditioning, belt 18 continues to advance in the direction of arrow 16. The photoreceptor belt 18 is first optionally exposed to a flood lamp 29 for erasing any residual charge therefrom, and then moved to a subsequent recharge station where another corona generating device 30 is utilized to recharge the photoconductor belt 18, having a first developed color separation thereon, to establish a new substantially uniform potential thereon. The belt then continues to travel to the next exposure station, where ROS 32 selectively dissipates the charge laid down by corotron 30 to record another color separated electrostatic latent image corresponding to regions to be developed with a magenta developer material. This color separated electrostatic latent image may be totally or partially superimposed on the image previously developed on the surface. Thereafter, the electrostatic latent image is advanced to the next successive coating flow applicator 34 which deposits magenta toner thereon.

After the electrostatic latent image has been developed with magenta toner, the photoconductive surface of belt 18 continues to be advanced to the next metering roll 36, to the next image conditioning station 38 and onward to flood lamp 39 and corona generating device 40, which, once again, recharges the photoconductive surface to a substantially uniform potential. Thereafter, ROS 42 selectively discharges this new charge potential on the photoconductive surface to record yet another color separated electrostatic latent image, which may be partially or totally superimposed on the prior cyan and magenta developed images, for development with yellow toner. In this manner, a yellow toner image is formed on the photoconductive surface of belt 18 in superimposed registration with the previously developed cyan and magenta images. It will be understood that the color of the toner particles at each development station may be provided in an arrangement and sequence that is different than described herein.

After the yellow toner image has been formed on the photoconductive surface of belt 18, the belt 18 continues to advance to the next metering roller 46, image conditioning station 48, and onward to flood lamp 49 and recharge station 50 and corresponding ROS 52 for selectively discharging those portions of belt 18 which are to be developed with black toner via a process known as black undercolor removal process wherein the developed image is located only on those portions of the photoconductive surface adapted to have black in the printed page and may not be superimposed over the prior cyan, magenta, and yellow developed images. This final developed image is once again metered and image conditioned at an image conditioning station 58 to compact the image and subsequently remove excess liquid from the image. Using the process described hereinabove, a composite multicolor toner image is formed on the photoconductive surface of belt 18. It will be recognized that the present description is directed toward a Recharge, Expose, and Develop (REaD) process, wherein the charged photoconductive surface of photoreceptive belt 18 is serially exposed to record a series of latent images thereon corresponding to the subtractive color of one of the colors of the appropriately colored toner particles at a corresponding development station. Thus, the photoconductive surface is continuously recharged and re-exposed to record latent images thereon corresponding to the subtractive primary of another color of the original. This latent image is therefore serially developed with appropriately colored toner particles until all the different color toner layers are deposited in superimposed registration with one another on the photoconductive surface. It should be noted that either discharged area development (DAD), wherein discharged portions are developed, or charged area development (CAD), wherein charged areas are developed can be employed.

After the composite multicolor image is formed on the photoreceptor, the multilayer developed image may be further conditioned with corona and/or light and then advanced to a transfer station, whereat a sheet of support material 100, typically a sheet of paper or some similar sheet like substrate, is guided into contact with the photoreceptor 18. At the transfer station, a corona generating device 108 directs ions onto the back side of the support material 100 for attracting the composite multicolor developed image on belt 18 to the support material 100. While direct transfer of the composite multicolor developed image to a sheet of paper has been described, one skilled in the art will appreciate that the developed image may be transferred to an intermediate member, such as a belt or drum, and then, subsequently, transferred and fused to the sheet of paper, as is well known in the art.

After the image has been transferred to the support substrate, a conveyor belt 110 moves the sheet of paper in the direction of arrow 112 to a drying or fusing station (not shown). The fusing station may include a heated roll in combination with a back-up or pressure roll, the rolls being resiliently urged into engagement with one another to form a nip through which the sheet of paper passes. The fusing station operates to affix the toner particles to the copy substrate so as to bond the multicolor image thereto. After fusing, the finished sheet is discharged and further transported for removal by the machine operator. Often, after the developed image is transferred from belt 18, residual developer material tends to remain, undesirably, on the surface thereof. In order to remove this residual toner from the surface of the belt 18, a cleaning roller 60, typically formed of an appropriate synthetic resin, is driven in a direction opposite to the direction of movement of belt 18 for contacting and cleaning the surface thereof. It will be understood that a number of photoconductor cleaning means exist in the art any of which would be suitable for use with the present invention.

The foregoing discussion provides a general description of the operation of a liquid developing material based electrostatographic printing machine incorporating a plurality of sensors in accordance with the present invention therein. The detailed structure of the series-capacitor sensors of the present invention will be described hereinafter with reference to FIGS. 1–6. It will be understood that the series-capacitor sensor of the present invention may be utilized in any liquid developing material-based printing machine, including multicolor or monocolor systems as well as systems wherein a latent image is created in a layer of liquid developing material with the image and background area subsequently separated to create a developed image. The developed image may be transferred directly to the copy sheet, as described, or to an intermediate member prior to transfer to the copy sheet. Multicolor printing machines may use this type of sensor where successive latent images are developed to form a composite multicolor toner image which is subsequently transferred to a copy sheet or, in lieu thereof, single color liquid images may be transferred in superimposed registration with one another directly to the copy sheet or to an intermediate transfer member in like manner. It will be understood that each series-capacitor sensor 62, 64, 66, and 68, shown in the apparatus of FIG. 7 is substantially identical.

The most convenient way of characterizing the electrical properties of liquid developers is by conductivity measurement facilitated by an induced low AC field (less than 10 volts/centimeter). While conductivity is an important parameter, it is the product of two components, namely, the charge density and mobility, that individually determine the efficiency of the development process. The traditional method of charge density and mobility measurements uses a sweep-out cell with a pair of parallel electrodes held at a constant voltage. However, neither the low AC field, or the constant voltage represents the actual development environment, where the field could be as high as $10^5$ volts/centimeter, and the voltage across the ink layer decreases in the millisecond time domain as the toner deposition progresses. Similarly, techniques based on transient optical phenomena have been implemented. The use of these techniques are usually limited to toner concentrations much lower than those in actual liquid developing material. Since liquid developing material properties are field and concentration dependent, such characterization methods do not reveal the true behavior of the materials in the actual development process.

The series-capacitor ink sensor of the present invention, unlike the methods described hereinabove, simulates the temporal and spatial variations of the electrical field in the development zone. This enables the variations of to properties more relevant to the development process to be detected.

Figure 1:
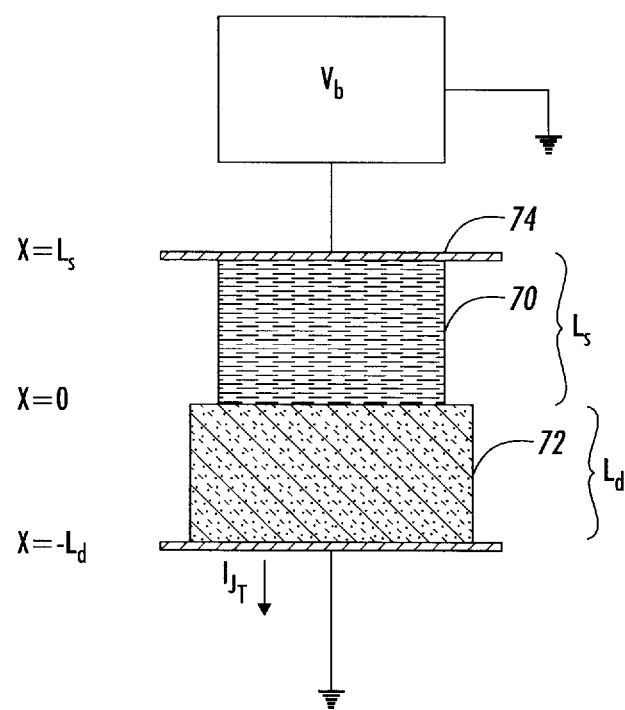
FIG. 1 is a schematic configuration for a series-capacitor discharge of liquid developer material samples according to the present invention.

Referring now to FIG. 1, there is shown a schematic configuration for a series-capacitor discharge of liquid developing material samples according to the present invention. In FIG. 1, a layer of liquid developing material 70 to be monitored is flanked by a grounded dielectric 72, which is a perfect capacitor acting as the surrogate photoreceptor in the dark, and a counter-electrode 74 held at a constant bias voltage $V_b$. It can be shown that the external current $J_T$ is a measure of the decay of voltage across the developing material layer 70 due to charge transport therein. While this phenomenon is essentially a dielectric relaxation, distinct features associated with space-charge-perturbed condition can arise from the low mobility and high charge density of the developing materials and the decaying voltage across the developing material layer. Although the present invention is directed to determining charge density and mobility in a liquid solution having electrically charged species therein, one skilled in the art will appreciate that the liquid solution includes collidal dispersions. Moreover, the electrically charged species include particles, counter-ions and co-ions.

Figure 2:
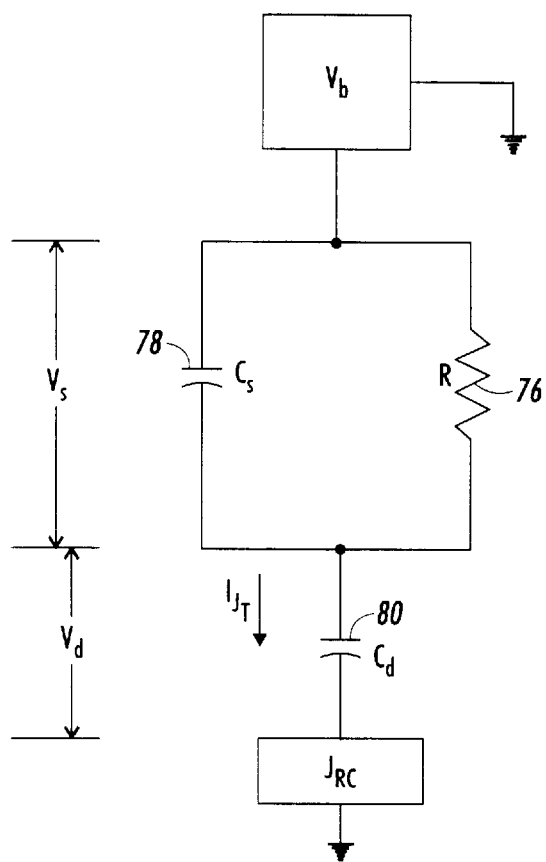
FIG. 2 is an equivalent electrical circuit diagram of FIG. 1.

FIG. 2 is an electrical equivalent circuit of dielectric relaxation in the series-capacitor configuration shown in FIG. 1. The transport properties of the system are represented by a sample resistance 76 (R) and capacitance's 78 and 80 of the sample ($C_s$) and the dielectric layers ($C_d$), respectively. The current density $J_{RC}$ as shown in FIG. 2 is given by, $$J_{RC}=(V_b/R)[C_d/(C_s+C_d)]^2\exp(-t/\tau) \tag{1}$$

where the relaxation time $\tau$ is, $$\tau=(C_s+C_d)R. \tag{2}$$

The resistance 76 is defined in terms of the charge density at equilibrium. In cases where charge transport becomes non-Ohmic, either due to a limited supply of charge species or the field being perturbed by the space-charge, the charge density could become non-uniform and differ significantly from the equilibrium value such that the concept of a well-defined "resistance" is no longer valid. In the following, the applicability of the above formulae is examined by deriving the current expression from the first principle charge transport theory.

In general, the total current density $J_T$ at a time t, for the system shown in FIGS. 1 and 2, can be written as the sum of conduction and displacement current densities as, $$J_T(t)=(\mu_p\rho_p+\mu_n\rho_n)E(x,t)+\in(\partial E/\partial t) \tag{3}$$

where E(x,t) is the electric field, $\in$ is the permitivity, $\rho$ is the volume density and $\mu$ is the mobilities of charge species. The subscripts p and n refer to the positive and the negative species, respectively.

Noting that there is no conduction current in a perfect capacitor (the "dielectric"), the separate integrations of Eq.(3) over the dielectric of thickness $L_d$ and the leaky capacitor (the "sample") of thickness $L_s$ yield, $$J_T(t) = -(\epsilon_d/L_d)(dV_d/dt) = \left[\int_0^{Ls} (\mu_p\rho_p + \mu_n\rho_n)Edx + \epsilon_s(dV_s/dt)\right]/L_s, \tag{4}$$

where $V_d$ and $V_s$ denote the voltages across the dielectric and the sample, respectively, and $\in_d$ and $\in_s$ are the permittivities of the dielectric and the sample, respectively. The time derivatives of V's can be eliminated from the condition that the sum of $V_d$ and $V_s$ equals to the constant bias voltage $V_b$, i.e., $$dV_d/dt+dV_s/dt=dV_b/dt=0. \tag{5}$$

Then, the total current density can be expressed as, $$J_T(t) = -[1/L_s(1 + C_s/C_d)] \int_0^{L_s} (\mu_p \rho_p + \mu_n \rho_n) E \, dx, \quad (6)$$

and the decay rates of voltages are given by, $$dV_s/dt = -dV_d/dt = -J_T/C_d, \quad (7)$$

where $C_s = \epsilon_s/L_s$ and $C_d = \epsilon_d/L_d$ are the capacitances of the sample and the dielectric, respectively. These results allow the calculations of the total current density $J_T$ and the layer voltages, $V_s$ and $V_d$, as functions of time using the instantaneous local values of charge densities $p(x,t)$'s and fields $E(x,t)$. The latter quantities can be obtained by solving the coupled continuity and Poisson's equations, which are given in one-dimensional geometry as, $$\partial \rho_p/\partial t = -(\partial/\partial x)(\mu_p \rho_p E) + g, \quad (8)$$

$$\partial \rho_n/\partial t = (\partial/\partial x)(\mu_n \rho_n E) - g, \quad (9)$$

$$\partial E/\partial x = (\rho_p + \rho_n)/\epsilon, \quad (10)$$

where g represents the rate of charge generation, which can be a function of position and time through its dependence on the local field $E(x,t)$.

The boundary conditions for these equations specify the interaction between the charge species in the sample layer and the electrodes. For example, in the case of inks one may assume that there is no charge exchange between the ink and the electrodes, hence, the densities of charge species are conserved in the ink layer. This is represented by the vanishing of outgoing conduction currents: for the positively charged species, $$J_p = \mu_p \rho_p E >= 0, \text{ at } x=0,$$

and $$J_p = \mu_p \rho_p E <= 0, \text{ at } x=L_s \quad (11)$$

and for the negatively charged species, $$J_n = \mu_n \rho_n E <= 0, \text{ at } x=0,$$

and $$J_n = \mu_n \rho_n E >= 0, \text{ at } x=L_s \quad (12)$$

Alternatively, the electrode at $x=L_s$ can be assumed to inject charge of the same polarity as the bias voltage at a rate which may depend on the field at $x=L_s$.

Another boundary condition is the continuity of displacements at the interface, $x=0$, $$\epsilon_s E(0) - \epsilon_d E_d = Q_s, \quad (13)$$

where $E_d = -V_d/L_d$ is the uniform electric field in the (space-charge free) dielectric. In the electrographic applications, $Q_s$ represents the latent image charge which is the driving force for electrophoresis. The field needed to drive the charge species is provided by the bias voltage $V_b$, and hence, the case for $Q_s = 0$ is considered.

The usual initial condition is that the sample is charge neutral with uniform distributions of positive and negative charge species, $$\rho_p(X,0) = -\rho_n(X,0) = \rho_o \text{ at all } X \text{ and } t=0, \quad (14)$$

hence, the initial field distribution is also uniform, $$E(X,0) = -V_b/L_s(1 + C_s/C_d) \text{ at all } X \text{ and } t=0. \quad (15)$$

The coupled equations, Eqs.(8, 9, 10) are solved numerically by the finite difference method. The numerical results are presented in a system of units with the sample thickness $L_s$, the permittivity $\epsilon_s$, the mobility of negative species $\mu_n$, and the charge density $\rho_o$ as the basic units. Other units can be derived from these four basic units as shown in Table I, together with the typical value of each unit. The derived units have important physical meanings. For example, the unit voltage $V_o$ corresponds to the voltage at which the total charge per unit area of sample $\rho_o L_s$ is equal to "one-CV's worth". The time unit $t_o$, is the transit time of negative species at the unit voltage and is also equal to the (intrinsic) dielectric relaxation time of the sample.

TABLE I

| System of Units and Typical Values | |
|---|---|
| Thickness: $L_s$ (of sample) | $5 \times 10^{-3}$ cm |
| Permittivity: $\epsilon_s$ (of sample) | $5 \times 10^{-13}$ F/cm |
| Charge mobility: $\mu_n$ (of negative species) | $10^{-4}$ cm$^2$/Vsec |
| Volume charge density: $\rho_o$ (in sample) | $10^{-5}$ Coul/cm$^3$ |
| Area charge density: $Q_o = \rho_o L_s$ | $5 \times 10^{-8}$ Coul./cm$^2$ |
| Voltage: $V_o = Q_o L_s/\epsilon_3 = \rho_o L_s^2/\epsilon_s$ | 500 V |
| Time: $t_o = L_s^2/\mu_n V_o = \epsilon_s/\mu_n \rho_o$ | $5 \times 10^{-4}$ sec |
| Current density: $J_o = Q_o/t_o = \mu_n \rho_o^2 L_s/\epsilon_s$ | $10^{-4}$ amp/cm$^2$ |

Turning now to FIG. 3, there is schematically shown a laboratory apparatus 10 designed to simulate the electrophoresis that occurs in liquid electrographic development. The apparatus 10 illustrated in FIG. 3, consists of two capacitors representing sample 70 and dielectric 72 connected in series. A constant bias voltage from a DC power supply 88 is applied to capacitor 70 by way of a fast acting relay switch 90. A coupling capacitor 82 connects capacitor 72 to an operational amplifier 84. The output of the amplifier 84 is connected to a visual output device 86, such as a cathode ray tube (CRT). Capacitor 72 is a perfect dielectric, which in electrographic applications, would be the imaging member bearing electrographic charges (i.e. the latent electrostatic images). The other capacitor 70 comprises the liquid ink sample system and consists of a film containing, for example, surfactant molecules in a hydrocarbon liquid with or without a dispersion of charged macroscopic particles of about 1 $\mu$m diameter. Although a power supply 88 provides a constant bias voltage applied to apparatus 10, the colloid-layer voltage in capacitor 70 decays as charged species move within the liquid sample. Thus, apparatus 10 allows for the observation of voltage decay, and the dielectric relaxation of a liquid developing material sample, by the measurement of external currents. Since this is a purely electrical measurement that does not involve optical detection, the technique is equally applicable to dispersions containing only the surfactant molecule and its aggregates, such as inverse micelles. Apparatus 10 provides a means for a comparative study of the electrical properties of dispersions with and without the presence of colloidal particles. However, because of the spatially uniform distribution of bipolar species, the technique is sensitive to the motion of all charges and cannot easily distinguish between the contributions of positive and negative species.

Referring further to FIG. 3, sheet 73 of 25 $\mu$m Mylar®, a registered trademark for a polyvinyl film material manufactured by E. I. DuPont de Nemours and Co. of Wilmington, Del., is placed on a polished aluminum block electrode 75 to form a "perfect" capacitor 72. A known amount of the liquid solution (approximately 0.13 cc) is placed on sheet 73 such that, upon covering it with another aluminum plate 77 (5×5 cm), the solution flows to fill the entire area of 25 cm². Knowing the carrier fluid density and weight of the solution, the thickness of the liquid layers formed is calculated to be approximately 60 $\mu$m. Some measurements were made using a cell giving liquid heights of approximately 125 $\mu$m. Although the total experimental time is typically much less than a minute, any possible complications due to settling out of colloidal particles on the sheet 73 of apparatus 10 out in the course of operation is avoided by using only fresh layers of solution for each measurement run.

The DC voltage is applied to capacitor 70 and relay 90 is activated by an external trigger on CRT 86, which is a Nicolet, Model Pro 10, oscilloscope. With the arrangement shown in FIG. 3, the change in the voltage across capacitor 70, and the related charge in the ink sample is measured and electronically differentiated by coupling capacitor 82 and amplifier 84 to yield the total current. With a variety of available sampling times (the shortest being 1 $\mu$sec) and employing different total numbers of points (up to 50 thousand), it is possible to measure the time-resolved current transients and integrated collected charge over a time range from $10^{-5}$ to $10^{-2}$ seconds.

FIG. 4 shows examples of experimental current versus time curves, obtained with a typical liquid developing material containing about 2% toner particles and about 0.1% charge directors in hydrocarbon liquid, at various bias voltages Vb. A comparison with the results of charge director solutions (containing no toners) identifies the first current peaks (at the shortest time) as due to the transit of toner particles. The toner mobility, together with the applied bias voltage, the liquid layer thickness and the properties of the dielectric, determines the transit time or the time when the current peaks appear.

The time integral of current from the curves of FIG. 4 provide a measure of the toner charge that can be collected within a period of time. Thus, changes in toner concentration or toner charge/mass ratio are reflected in the current integral versus time relations shown in FIG. 5. A decrease in the toner concentration without significant decrease in the charge/mass ratio, (and hence, the mobility), causes the saturation level of the integral to decrease but without much delay in the saturation time. On the other hand, a change in the charge/mass ratio, (and hence, the mobility), results in a decreased saturation value and delayed saturation time. Thus, a decrease in the current integral value measured at a time comparable to the development time is a signal of the potential for insufficient DMA (development mass per area) because of changes in liquid developing material performance and the need for adjustments to developing material composition or development process parameters.

Turning now to FIG. 6, there is shown schematically a series-capacitor sensor 12 based upon the laboratory apparatus 10 discussed hereinabove with reference to FIG. 3. Sensor 12 is intended for use in the printing machine discussed with reference to FIG. 7. The sensor 12 comprises a pair of concentric cylinders 94 and 96. A dielectric layer 98 is coated on the inner surface of cylinder 94 to form the "perfect" capacitor. A sample of liquid developing material flows into sensor 12. An electrode 93 coaxial with cylinders 94 and 96 connects to a DC power supply 88 through a fast acting relay 90. Electrode 93 conveys a voltage to the ink sample. The outer surface of cylinder 94 is connected to one plate of coupling capacitor 82. The other plate of capacitor 82 connects to an inverting input 81 of operational amplifier 84. In this manner, the voltage across the liquid developing material sample is conveyed to amplifier 84 for measurement thereof. A noninverting input 83 of operational amplifier 84 is grounded. A feedback resistor 89, connected between input 81 and output terminal 85, returns a portion of an output voltage to input 81 that is out of phase with the input voltage. Feedback resistor 89, coupling capacitor 82, and operational amplifier 84 form a differentiating circuit such that the output signal thereof is proportional to the rate-of-change of the input signal. An indicator 87 is connected between output terminal 85 and ground, and triggered by power supply 88 through a conductor 91. The present invention comprises a series-capacitor sensor that monitors the voltage decay and relaxation of a liquid developing material sample by measuring external currents. When there is a change in the liquid developing material performance, the sensor activates external devices to adjust the liquid developing material composition or the development process.

In review, the present invention provides an apparatus for determining charge density and mobility in a liquid solution having electrically charged particles therein. The apparatus includes, an electrode. A dielectric member having a first surface situated opposite the electrode provides for a volume therebetween in which a sample of the liquid may be placed. A fixed bias voltage is applied to the electrode to produce an electrical current flow through the liquid solution and the dielectric member. Means coupled to the dielectric member measure the electrical current as a function of time to provide a measure of voltage decay across the liquid solution. The voltage decay corresponds to the charge density of the liquid solution.

It is, therefore, apparent that there has been provided, in accordance with the present invention, series-capacitor in sensor for liquid developers. This apparatus fully satisfies the aspects of the invention hereinbefore set forth. While this invention has been described in conjunction with specific embodiments thereof, it is evident that many alternatives, modifications and variations will be apparent to those skilled in the art. Accordingly, it is intended to embrace all such alternatives, modifications, and variations as fall within the spirit and broad scope of the appended claims.

We claim:

1. An apparatus for determining charge density and mobility in a liquid solution having electrically charged species therein, comprising:

an electrode;

a dielectric member having a first surface situated opposite said electrode for providing a volume therebetween in which a sample of the liquid solution may be placed;

means for applying a fixed bias voltage to said electrode so as to produce an electrical current flow through the liquid solution and said dielectric member;

means, coupled to said dielectric member, for measuring the electrical current flow as a function of time to provide a measure of voltage decay across the liquid solution, wherein said voltage decay corresponds to the charge density of the liquid solution, and wherein said means for measuring the electrical current includes a differentiator, the differentiator comprising:

an operational amplifier having an inverting input, a non-inverting input, and an output, wherein said non-inverting input is connected to ground;

an indicator connected between said output and a ground potential, wherein said indicator is triggered by said fixed bias voltage applying means;

a coupling capacitor having a first termination and a second termination, wherein said coupling capacitor first termination is connected to said inverting input, and said coupling capacitor second termination is connected to said dielectric member for coupling an input voltage to said inverting input;

a feedback resistor having a first termination and a second termination, wherein said feedback resistor first termination is connected to said output, and said feedback resistor second termination is connected to said inverting input for returning a portion of an output voltage to said inverting input; and wherein said feedback resistor and said coupling capacitor are defined by preselected parameters for generating said output voltage such that said output voltage is out of phase with said input voltage and proportional to a rate of change thereof.

2. An apparatus according to claim 1, wherein said liquid solution includes a colloidal dispersion.

3. An apparatus according to claim 1, wherein said electrically charged species include particles, counter-ions and co-ions.

4. An apparatus according to claim 1, wherein said fixed bias voltage applying means comprises:

a DC power supply having an output terminal; and a switch connected between said output terminal and said electrode.

5. A sensor for determining charge density and mobility in a liquid developer comprising liquid carrier and electrically charged toner particles therein, comprising:

an electrode;

a dielectric member having a first surface situated opposite said electrode for providing volume therebetween in which a sample of the liquid developer may be placed, wherein said dielectric member comprises a dielectric layer located between a first concentric cylinder and a second concentric cylinder;

mean for applying a fixed bias voltage to said electrode so as to produce an electrical current through the liquid developer and said dielectric member; and means, coupled to said dielectric member, for measuring the electrical current as a function of time to provide a measure of voltage decay across the liquid developer, wherein said voltage decay corresponds to the charge density of the liquid developer.

6. A sensor according to claim 5 wherein said electrode is coaxial with said dielectric member.

7. A sensor for determining charge density and mobility in liquid developer comprising liquid carrier and electrically charged toner particles therein, comprising:

an electrode;

a dielectric member having a first surface situated opposite said electrode for providing a volume therebetween in which a sample of the liquid developer may be placed;

means for applying a fixed bias voltage to said electrode so as to produce an electrical current through the liquid developer and said dielectric member; and means, coupled to said dielectric member, for measuring the electrical currents as a function of time to provide a measure of voltage decay across the liquid developer, wherein said voltage decay corresponds to the charge density of the liquid developer, wherein said means for measuring the electrical current includes a differentiator, the differentiator comprising:

an operational amplifier having an inverting input, a non-inverting input, and an output, wherein said non-inverting input is connected to ground;

an indicator connected between said output and a ground potential, wherein said indicator is triggered by said fixed bias voltage applying means;

a coupling capacitor having a first termination and a second termination, wherein said coupling capacitor first termination is connected to said inverting input, and said coupling capacitor second termination is connected to said dielectric member for coupling an input voltage to said inverting input;

a feedback resistor having a first termination and a second termination, wherein said feedback resistor first termination is connected to said output, and said feedback resistor second termination is connected to said inverting input for returning a portion of an output voltage to said inverting input; and wherein said feedback resistor and said coupling capacitor are defined by preselected parameters for generating said output voltage such that said output voltage is out of phase with said input voltage and proportional to a rate of change thereof.

8. A sensor according to claim 7, wherein said indicator is operative to adjust said liquid developer in response to detecting a physical change in said liquid developer.

9. An electrostatographic printing machine of the type having a liquid developer including liquid carrier and electrically charged toned particles therein, said printing machine including a sensor for determining charge density and mobility in the liquid developer, comprising:

an electrode;

a dielectric member having a first surface situated opposite said electrode for providing a volume therebetween in which a sample of the liquid developer may be placed, wherein said dielectric member comprises a dielectric layer located between a first concentric cylinder and a second concentric cylinder;

means for applying fixed bias voltage to said electrode so as to produce an electrical current through the liquid developer and said dielectric member; and means coupled to said dielectric member, for measuring the electrical current as a function of time to provide a measure of voltage decay across the liquid developer, wherein said voltage decay corresponds to the charge density of the liquid developer.

10. A printing machine according to claim 9 wherein said electrode is coaxial with said dielectric member.

11. An electrostatographic printing machine of the type having liquid developer including liquid carrier and electrically charged toner particles therein, said printing machine including a sensor for determining charge density and mobility in the liquid developer comprising:

an electrode;

a dielectric member having a first surface situated opposite said electrode for providing a volume therebetween in which a sample of the liquid developer may be placed;

means for applying a fixed bias voltage to said electrode so as to produce an electrical current through the liquid and said dielectric member; and means coupled to said dielectric members, for measuring the electrical current as a function of time to provide a measure of voltage decay across the liquid developer, wherein said voltage decay corresponds to the charge density of the liquid developer, wherein said means for measuring the electrical current includes a differentiator, the differentiator comprising:

an operational amplifier having an inverting input, a non-inverting input, and an output, wherein said non-inverting input is connected to ground;

an indicator connected between said output and a ground potential, wherein said indicator is triggered by said fixed bias voltage applying means;

a coupling capacitor having a first termination and a second termination, wherein said coupling capacitor first termination is connected to said inverting input, and said coupling capacitor second termination is connected to said dielectric member for coupling an input voltage to said inverting input;

a feedback resistor having a first termination and a second termination, wherein said feedback resistor first termination is connected to said output, and said feedback resistor second termination is connected to said inverting input for returning a portion of an output voltage to said inverting input; and wherein said feedback resistor and said coupling capacitor are defined by preselected parameters for generating said output voltage such that said output voltage is out of phase with said input voltage and proportional to a rate of change thereof.

12. A printing machine according to claim 11, wherein said indicator is operative to adjust said liquid developer in response to a predetermined change in said liquid developer charge or mobility.

* * * * *